US011672436B2

(12) United States Patent
Balakrishnan et al.

(10) Patent No.: US 11,672,436 B2
(45) Date of Patent: Jun. 13, 2023

(54) PULSE DETECTION FROM HEAD MOTIONS IN VIDEO

(71) Applicant: Massachusetts Institute of Technology, Cambridge, MA (US)

(72) Inventors: Guha Balakrishnan, Cambridge, MA (US); John V. Guttag, Lexington, MA (US); Frederic Durand, Somerville, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 364 days.

(21) Appl. No.: 16/824,206

(22) Filed: Mar. 19, 2020

(65) Prior Publication Data

US 2020/0214575 A1 Jul. 9, 2020

Related U.S. Application Data

(63) Continuation of application No. 14/315,174, filed on Jun. 25, 2014, now Pat. No. 10,638,942.

(60) Provisional application No. 61/839,563, filed on Jun. 26, 2013.

(51) Int. Cl.
*A61B 5/024* (2006.01)
*A61B 5/0255* (2006.01)
*A61B 5/11* (2006.01)
*A61B 5/00* (2006.01)

(52) U.S. Cl.
CPC .............. *A61B 5/024* (2013.01); *A61B 5/004* (2013.01); *A61B 5/0255* (2013.01); *A61B 5/1128* (2013.01)

(58) Field of Classification Search
CPC ....... A61B 5/024; A61B 5/004; A61B 5/0255; A61B 5/1128
See application file for complete search history.

(56) References Cited

U.S. PATENT DOCUMENTS

| 6,056,671 A | 5/2000 | Marmer |
| 10,638,942 B2 | 5/2020 | Balakrishnan |
| 2013/0281830 A1* | 10/2013 | Patz ...................... A61B 5/024 600/419 |

(Continued)

OTHER PUBLICATIONS

Poh, M. et al. "Non-contact automated cardiac pulse measurements using video imaging and blind source separation," Optics Express, 18(10): 10762-10774 (2010) (Year: 2010).*

(Continued)

*Primary Examiner* — Joseph M Dietrich
(74) *Attorney, Agent, or Firm* — Hamilton, Brook, Smith & Reynolds, P.C.

(57) ABSTRACT

Heart rates and beat lengths of a subject can be extracted from videos of the subject by measuring subtle head motion caused by the Newtonian reaction to the influx of blood at each beat. Embodiments track features on the video images of the subject's head and perform principal component analysis (PCA) to decompose the feature location-time series into a set of component motions. The method or system then selects a component that best corresponds to heartbeats based on its temporal frequency spectrum. Finally, the motion projected to this component is analyzed and peaks of the location-time series are identified, which correspond to heartbeats. Pulse rate measurements or heart rate measurements of the subject are output.

20 Claims, 9 Drawing Sheets

(56) References Cited

U.S. PATENT DOCUMENTS

| | | |
|---|---|---|
| 2014/0072190 A1 | 3/2014 | Wu |
| 2014/0072228 A1 | 3/2014 | Rubinstein |
| 2014/0072229 A1 | 3/2014 | Wadhwa |
| 2014/0180132 A1 | 6/2014 | Shan |

OTHER PUBLICATIONS

Adde, L. et al. "Early prediction of cerebral palsy by computer-based video analysis of general movements: a feasibility study," Developmental Medicine & Child Neurology, 52: 773-778 (2010).
Bonmassar, G. et al., "Motion and ballistocardiogram artifact removal for interleaved recording of EEG and EPS during MRI," Neuroimage, 16: 1127-1 141 (2001).
Bradski, G., "The Open CV Library," Dr. Dobb's Journal of Software Tools (2000).
Chen, S. et al., "Quantification and recognition of parkinsonian gait from monocular video imaging using kernel based principal component analysis," BioMedical Engineering OnLine, 10 (2011).
Delano, M., "A long term wearable electrocardiogram (ECG) measurement system," Master's Thesis, Massachusetts Institute of Technology (2012).
Garbey, M. et al., "Contact-free measurement of cardiac pulse based on the analysis of thermal imagery," IEEE Trans Biomed Eng, 54(8): 1418-1426 (2007).
He, D. et al., "A continuous, wearable, and wireless heart monitor using head ballistocardiogram (bcg) and head electrocardiogram (ecg)," Conf Proc IEEE Eng Med Biol Soc. 2011 (2011).
Inan, O. et al., "Robust ballistocardiogtam acquisition for home monitoring," Physiological Measurement, 30: 169-185 (2009).
Kim, K. et al., "A new method for unconstrained pulse arrival time measurement on a chair," J. Biomed. Eng. Res., 27:83-88 (2006).
Liu, C. et al., "Motion magnification," ACM Trans. Graph., 24(3): 519-526 (2005).
Lynch, P., "Human head anatomy with external and internal carotid arteries," http://www.flickr.com/photos/patrlynch/450142019/, Apr. 2007.
Pediaditis, M. et al., "Vision-based human motion analysis in epilepsy—methods and challenges," Proceedings of IEEE ITAB, pp. 1-5 (2010).
Phillips, Philips vital signs camera, http://www.vitalsignscamera.com, 2011.
Poh, M. et al., "Non-contact, automated cardiac pulse measurements using video imaging and blind source separation," Optics Express, 18(10): 10762-10774 (2010).
Starr, I. et al., "Studies on the estimation of cardiac output in man, and of abnormalities in cardiac function, from the hearts recoil and the bloods impacts; the ballistocardiogram," The American Journal of Physiology, 127: 1-28 (1939).
Syed, Z. et al. "Computationally generated cardiac biomarkers for risk stratification after acute coronary syndrome," Sci Trans. Med, 3(102): 102ra95 (2011).
Tan, K. et al., Real-time vision based respiration monitoring system. Proceedings of CSNDSP, pp. 770-774 (2010).
Verkruysse, W. et al., "Remote plethysmographic imaging using ambient light," Optics Express, 16(26): 21434-21445 (2008).
Viola, P. and M. Jones, "Rapid object detection using a boosted cascade of simple features," Proceedings of IEEE Conference on Computer Vision and Pattern Recognition, pp. 511-518 (2001).
Wang, C. et al. "Vision analysis in detecting abnormal breathing activity in application to diagnosis of obstructive sleep apnoea," Proceedings of IEEE Eng Med Biol Soc, pp. 4469-4473 (2006).
Wieringa, F. et al., "Contactless multiple wavelength photoplethysmogtaphic imaging: a first step toward SpO2 camera technology," Ann. Biomed. Eng., 33(8): 1034-1041 (2005).
Wu, H. et al., "Eulerian video magnification for revealing subtle changes in the world," ACM Trans. Graph. (Proceedings SIGGRAPH 2012), 31(4) (2012).

* cited by examiner

PULSE DETECTION FROM HEAD MOTIONS IN VIDEO

RELATED APPLICATION

This application is a continuation of U.S. application Ser. No. 14/315,174, filed Jun. 25, 2014, which claims the benefit of U.S. Provisional Application No. 61/839,563, filed Jun. 26, 2013. The entire teachings of the above applications are incorporated herein by reference.

BACKGROUND

Head movements that are related to cardiac activity are small and mixed in with a variety of other involuntary head movements. From a biomechanical standpoint, the head-neck system and the trunk can be considered as a sequence of stacked inverted pendulums. This structure allows the head unconstrained movement in most axes.

SUMMARY

Several sources of involuntary head movement can complicate the isolation of movements attributable to pulsatile activity. One is the pendular oscillatory motion that keeps the head in dynamic equilibrium. (He, D. et al., "A continuous, wearable, and wireless heart monitor using head ballistocardiogram (bcg) and head electrocardiogram (ecg)," Conf Proc IEEE Eng Med Biol Soc. 2011 (2011). (Hereinafter, "He, D., et al.")). A second source of involuntary head movement is the bobbing caused by respiration.

The heart is a hollow muscle that pumps blood throughout the body by re-peated, cyclical contractions. The heart is composed of four chambers: the left ventricle, right ventricle the left atrium, and the right atrium. During the phase of the cardiac cycle known as diastole, the ventricles relax and allow blood to flow into them from the atria. In the next phase known as systole, the ventricles contract and pump blood to the pulmonary artery and aorta. The aorta, in turn, transports blood to the rest of the body. The head and neck receive blood from the aorta via the common carotid arteries, which further divide into the internal and external carotid arteries in the neck. However, from a biomechanical standpoint, the head-neck system and the trunk can be considered as a sequence of stacked inverted pendulums. This structure allows the head unconstrained movement in most axes, making calculations of the system's motion complicated.

It is uncertain how much detected head motion is attributable to the large acceleration of blood in the aorta compared to the localized acceleration of blood in the carotid arteries moving into the head. He, D, measured ballistocardiac head motions with an accelerometer-based device to be on the order of $$10 \text{ mG} \left(0.098 \frac{m}{s^2}\right),$$

but it is unclear how much of this movement is attributed to aortic and carotid blood flow forces.

During systole, a healthy adult aorta is capable of impelling a volume of 70-80 ml (0.07-0.08 kg) of blood at considerable speed $$\left(1 \frac{m}{s}\right)$$

and acceleration $$\left(20 \frac{m}{s^2}\right).$$

An average adult male weighs 70 kg. Using Newton's 2nd and 3rd laws, the approximate acceleration of the body due to the aortic forces ($a_{body}$) can be derived:

$$|F_{body}| = |F_{blood}|$$
$$|a_{body} * m_{body}| = |a_{blood} * m_{blood}|$$
$$|a_{body} * 70 \text{ kg}| = 20 \frac{m}{s^2} * 0.07 \text{ kg}$$
$$|a_{body}| = 0.02 \frac{m}{s^2}$$

Thus, the approximate acceleration of the body due to the aortic forces is $$0.02 \frac{m}{s^2}.$$

In addition to aortic blood acceleration, there is a smaller force resulting from blood flowing through the carotid arteries into the head. Although there are studies measuring blood flow, velocity and acceleration of blood in the carotid, experimental measurements on the force imparted by carotid blood flow on the head have not been found. According to one study, blood velocity in the common carotid increases from approximately $$0.02 \frac{m}{s} \text{ to } 0.11 \frac{m}{s}$$

in 0.1 s, or an acceleration of $$0.9 \frac{m}{s^2}.$$

The blood mass transported in this period is roughly 13 ml or 0.013 kg. Assuming both carotid arteries are identical and that the head is 5 kg, we use a similar derivation to the one used in Section 2.1.1 to find that the head should accelerate roughly $$0.005 \frac{m}{s^2}$$

assuming independence from the rest of the body.

Pulse rate captures the average number of cardiac cycles over a period of time (e.g., 30 seconds), which is useful primarily for detecting acute problems. There is a growing body of evidence that measuring beat-to-beat variations provides additional in-formation with long-term prognostic value. The most established of these measures is heart rate variability (HRV). HRV measures the variation in the length of individual normal (sinus) heartbeats and provides an indication of the degree to which the sympathetic and parasymathetic nervous systems modulate cardiac activity. To measure HRV, the interarrival times of beats must be accurately measured, which can be determined by locating the "R" peaks in successive beats in an ECG. A lack of sufficient variation when the subject is at rest suggests that the nervous system may not perform well under stress. Patients with decreased HRV are at an increased risk of adverse outcomes such as fatal arrhythmias.

Pulse rate captures the average heart rate over a period of time (e.g., 30 seconds). It is useful primarily for detecting acute problems. A growing body of evidence shows that measuring beat-to-beat variations provides additional information with long-term prognostic value. (Syed, Z. et al., "Computationally generated cardiac biomarkers for risk stratification after acute coronary syndrome," *Sci. Trans. Med.*, 3(102):102ra95 (2011).. (Hereinafter, "Syed, Z. et al.")) The most established of these measures is heart rate variability (HRV). HRV measures the variation in the length of individual normal (sinus) heartbeats. HRV provides an indication of the degree to which the sympathetic and parasympathetic nervous systems are modulating cardiac activity. To measure HRV, the interarrival times of beats are accurately measured, which can be determined by locating "R" peaks in successive beats in an ECG. A lack of sufficient variation when the subject is at rest suggests that the nervous system may not perform well under stress. Patients with decreased HRV are at an increased risk of adverse outcomes such as fatal arrhythmias.

Heart rate is a critical vital sign for medical diagnosis. Extracting heart rate without physically contacting the patient is desirable, particularly for populations such as premature neonates and the elderly for whom the skin is fragile and damageable by traditional sensors. Furthermore, for the elderly demographic, continuous, or at least frequent, monitoring outside of clinical environments can provide doctors with timely samples, long-term trends, and statistical analyses. Acceptance of such monitoring depends in part on the monitors being non-invasive and non-obtrusive.

In an embodiment of the present invention, subtle head oscillations that accompany the cardiac cycle are exploited to extract information about cardiac activity from videos. In addition to unobtrusively measuring heart rate, the method can extract other clinically useful information about cardiac activity, such as subtle changes in the length of heartbeats that are associated with the health of the autonomic nervous system.

In an embodiment, a method includes selecting a region of a video, tracking features of the selected region of the video, and analyzing the features of the selected region of the video to determine an oscillation rate of a subject shown in the video.

In an embodiment, the oscillation rate is a heart rate or pulse rate of the subject.

In an embodiment, the method includes extracting a component of the tracked features of the subject video. The extracted component can be a vertical component, horizontal component, or both vertical and horizontal components. However, a person of ordinary skill in the art can recognize the extracted component(s) can have a different orientation based on the input video.

In an embodiment, selecting the region of the video includes finding a region of interest including a head of a subject.

In an embodiment, tracking the features includes determining a maximum distance traveled by each point between consecutive frames of the video and discarding features corresponding to points having a distance in consecutive frames of the video exceeding a mode of distribution.

In an embodiment, analyzing the features can include filtering the extracted features temporally. Analyzing the features can further include generating a plurality of components using principal component analysis on the temporally filtered extracted features. Analyzing the features can include selecting one of the components of the plurality of components generated by the principal component analysis. Analyzing the features can further include detecting peaks of the selected component. Analyzing the features can further include determining the oscillation rate based on the detected peaks of the selected component.

In an embodiment, filtering the extracted features temporally can remove frequencies that are outside a predetermined range of pulse rates.

In an embodiment, performing principal component analysis can include decomposing the filtered features into a set of independent source signals.

In an embodiment, selecting the component includes selecting the component having a clearest main frequency.

In an embodiment, a system can include a selection module configured to select a region of a video, a tracking module configured to track features of the selected region of the video, and an analysis module the features of the selected region of the video to determine an oscillation rate of a subject shown in the video.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

In an embodiment of the present invention, a method takes an input video of a person's head and returns a pulse rate as well as a series of beat locations which can be used for the analysis of beat-to-beat variability. Feature tracking extracts the motion of the head. The method then isolates the motion corresponding to the pulse and projects it onto a 1D signal that allows us to extract individual beat boundaries from the peaks of the trajectory. For this, the method uses PCA and selects the component whose temporal power spectrum best matches a pulse. The method projects the trajectories of feature points onto this component and extract the beat locations as local extrema.

Figure 1:
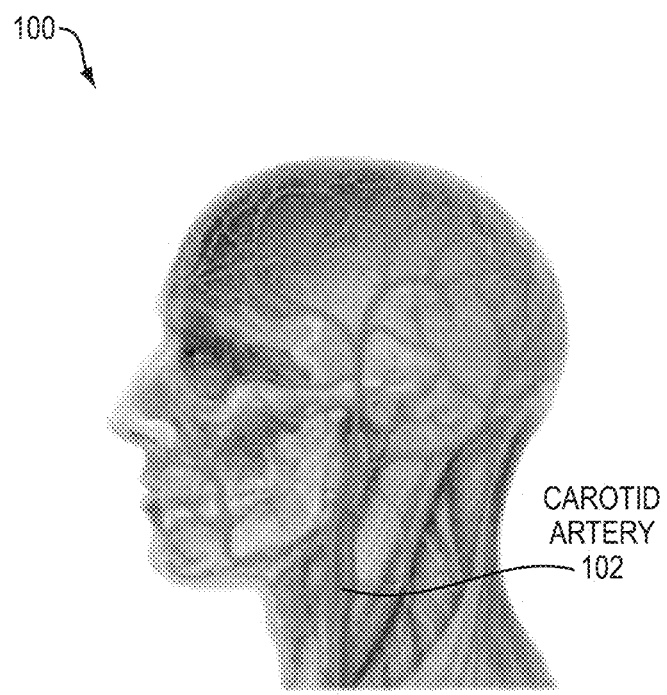
FIG. 1 is a diagram showing the cyclical movement of blood from the heart to the head via the abdominal aorta and the carotid arteries that cause the head to move in a periodic motion.

FIG. 1 is a diagram 100 showing the cyclical movement of blood from the heart to the head via the abdominal aorta and the carotid arteries 102 that cause the head to move in a periodic motion. Blood can flow from the heart to the head via the carotid arteries on either side of the head. In an embodiment of the present invention, a method detects pulse from this movement by tracking feature points on a person's head, filtering velocities by a temporal frequency band of interest, and using principal component analysis ("PCA") to find a periodic signal caused by pulse. The method extracts an average pulse rate from this signal by examining its frequency spectrum and obtains precise beat locations with a simple peak detection algorithm.

The method complements the extraction of pulse rate from video via analysis of the subtle color changes in the skin caused by blood circulation (Poh, M. et al., "Non-contact, automated cardiac pulse measurements using video imaging and blind source separation," *Optics Express*, 18(10): 10762-10774 (2010)) (Hereinafter, "Poh"); (Verkruysse, W. et al., "Remote plethysmographic imaging using ambient light," *Optics Express*, 16(26): 21434-21445 (2008)) (Hereinafter, "Verkruysse"). The methods described in Poh and Verkruysse average pixel values for all channels in the facial region and temporally filter the signals to an appropriate band. The method of Verkruysse uses these signals directly for analysis, while the method of Poh performs ICA to extract a single pulse wave. Both find the frequency of maximal power in the frequency spectrum to provide a pulse estimate.

Philips also produces a commercial application that detects pulse from color changes in real-time (Phillips, Philips vital signs camera, http://www.vitalsignscamera.com, 2011). (Hereinafter, "Phillips")). These color-based detection schemes require facial skin to be exposed to the camera. In contrast, an embodiment of the present invention is not restricted to a particular view of the head, and is effective even when skin is not visible. Non-invasive pulse estimation using modalities other than video such as thermal imagery (Garbey, M. et al., "Contact-free measurement of cardiac pulse based on the analysis of thermal imagery," *IEEE Trans Biomed Eng*, 54(8):1418-1426 (2007) (Hereinafter, "Garbey")) and photoplethysmography (measurement of the variations in transmitted or reflected light in the skin. (Wieringa, F. et al., "Contactless multiple wavelength photoplethysmogtaphic imaging: a first step toward $SpO_2$ camera technology," *Ann. Biomed. Eng.*, 33(8): 1034-1041 (2005). (Hereinafter, "Wieringa")).

Body motion in videos can be analyzed in different medical contexts, such as the measurement of respiration rate from chest movement (Tan, K. et al., "Real-time vision based respiration monitoring system." *Proceedings of CSNDSP*, pages 770-774 (2010). (Hereinafter, "Tan".); (Phillips), or the monitoring of sleep apnea by recognizing abnormal respiration patterns (Wang, C. et al. "Vision analysis in detecting abnormal breathing activity in application to diagnosis of obstructive sleep apnoea," *Proceedings of IEEE Eng Med Biol Soc*, pages 4469-4473 (2006). (Hereinafter, "Wang")). Motion studies for diseases include identification of gait patterns of patients with Parkinson's disease (Chen, S. et al., "Quantification and recognition of parkinsonian gait from monocular video imaging using kernelbased principal component analysis," *BioMedical Engineering OnLine*, #10 (2011). (Hereinafter, "Chen")), detection of seizures for patients with epilepsy (Pediaditis, M. et al., "Vision-based human motion analysis in epilepsy—methods and challenges," *Proceedings of IEEE ITAB*, pages 1-5 (2010). (Hereinafter, "Pediaditis")) and early prediction of cerebral palsy (Adde, L. et al. "Early prediction of cerebral palsy by computer-based video analysis of general movements: a feasibility study," *Developmental Medicine & Child Neurology*, 52: 773-778 (2010). (Hereinafter, "Adde")). The movements involved in these approaches tend to be larger in amplitude than the involuntary head movements due to the pulse.

Imperceptible motions in video can also be amplified (Wu, H. et al., "Eulerian video magnification for revealing subtle changes in the world," *ACM Trans. Graph.* (*Proceedings SIGGRAPH 2012*), 31(4) (2012). (Hereinafter, "Wu"); Liu, C. et al., "Motion magnification," *ACM Trans. Graph.*, 24(3):519-526 (2005) (Hereinafter, "Liu")). See also Wu et al., "Linear-Based Eulerian Motion Modulation," U.S. patent application Ser. No. 13/850,717, Wadhwa et al., "Complex-Valued Phase-Based Eulerian Motion Modulation," U.S. application Ser. No. 13/707,451 and Rubinstein et al., "Complex-Valued Eulerian Motion Modulation," U.S. application Ser. No. 13/607,173, which are all hereinafter incorporated by reference in their entirety. While these methods make small motions visible, the goal of the embodiments of the present invention is to extract quantitative information about heartbeats.

Using Newton's Third Law of Motion to measure cardiac activity dates back to at least the 1930s in using ballistocardiogram (BCG) (Starr, I. et al., "Studies on the estimation of cardiac output in man, and of abnormalities in cardiac function, from the hearts recoil and the bloods impacts; the ballistocardiogram," *The American Journal of Physiology*, 127: 1-28 (1939). (Hereinafter, "Starr")). A subject can be placed on a low-friction platform, and the displacement of the platform due to cardiac activity can be measured. The BCG is not widely used anymore in clinical settings. Other clinical methods using a pneumatic chair and strain sensing foot scale have also been successful under laboratory conditions (Kim, K. et al., "A new method for unconstrained pulse arrival time measurement on a chair," *J. Biomed. Eng. Res.*, 27: 83-88 (2006). (Hereinafter, "Kim"); Inan, 0. et al., "Robust ballistocardiogtam acquisition for home monitoring," *Physiological Measurement*, 30: 169-185 (2009). (Hereinafter, "Inan")). Ballistocardiographic head movement of the sort studied here has generally gained less attention. Such movement has been reported during studies of vestibular activity and as an unwanted artifact during MRI studies (Bonmassar, G. et al., "Motion and ballistocardiogram artifact removal for interleaved recording of EEG and EPS during MRI," *Neurolmage*, 16: 1127-1 141 (2001). (Hereinafter, "Bonmassar")). Recently, He, et al. proposed exploiting head motion measured by accelerometers for heart rate monitoring as a proxy for traditional BCG.

An embodiment of the present invention extracts a pulse rate and series of beat sequences from video recordings of head motion. Then, the method evaluates the extracted heart rate and beat location measurements on subjects against an electrocardiogram. Results show that the present method extracts accurate heart rates and can capture clinically relevant variability in cardiac activity.

Figure 2:
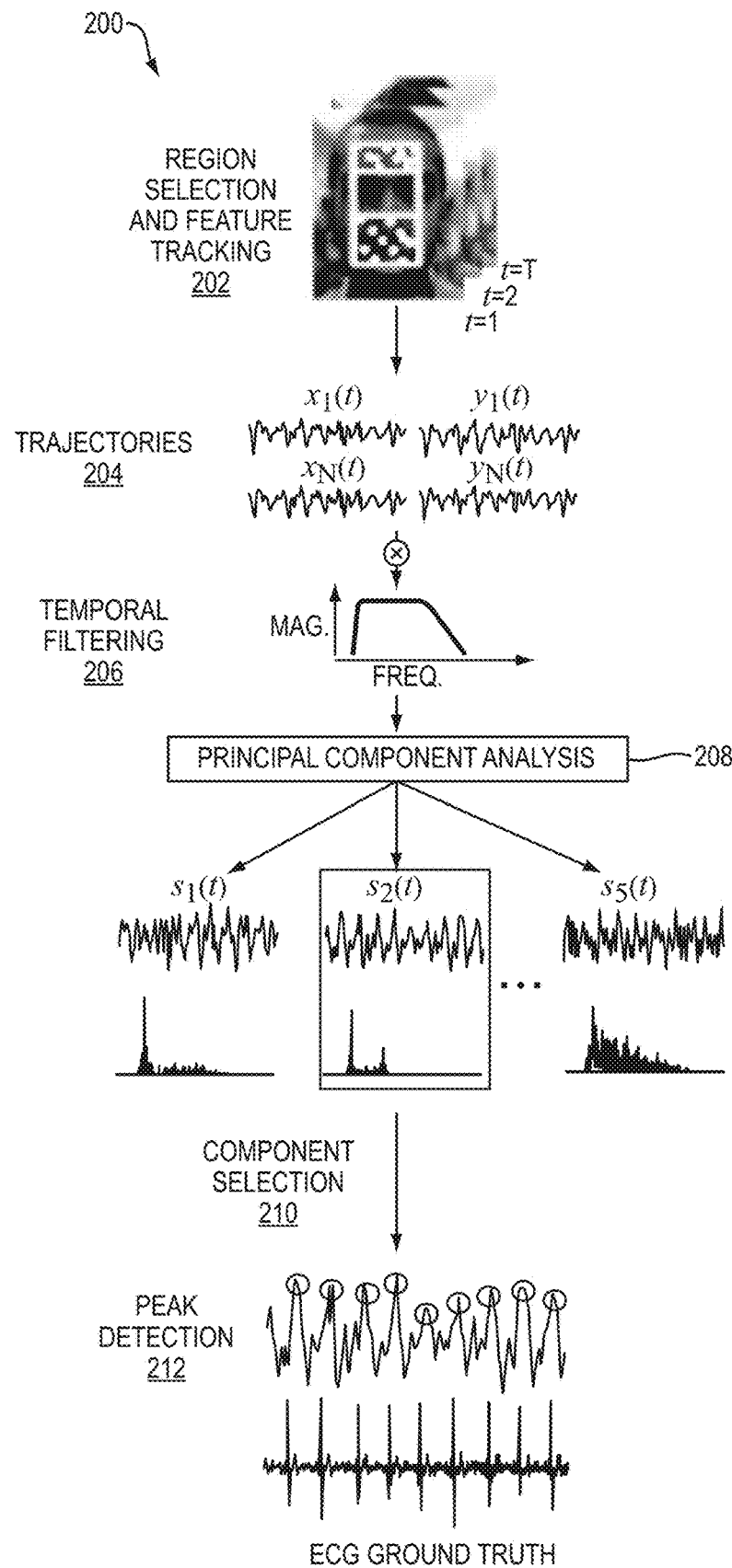
FIG. 2 is a flow diagram illustrating a high level overview of an embodiment of the present invention.

FIG. 2 is a flow diagram 200 illustrating a high level overview of an embodiment of the present invention. The recorded subject is assembled to be stationary and sitting upright for the duration of the video. First, a region is selected within the head by locating the head region and feature points are tracked for all frames (t=1 . . . T) of the video (202). The method finds a region of interest containing the head and track feature points within the region (e.g., 202). For videos where the front of the face is visible, the method can use the Viola Jones face detector (Viola, P. and M. Jones, "Rapid object detection using a boosted cascade of simple features," *Proceedings of IEEE Conference on Computer Vision and Pattern Recognition*, pages 511-518 (2001). (Hereinafter, "Viola")) from OpenCV 2.4 (Bradski, G., "The Open CV Library," *Dr. Dobb's Journal of Software Tools* (2000). (Hereinafter, "Bradski")) to first find a rectangle containing the face. The method can use the middle 50% of the rectangle widthwise and 90% heightwise from top in order to ensure the entire rectangle is within the facial region. The method also removes the eyes from the region so that blinking artifacts do not affect the results. To do this, the method can remove subrectangle (e.g., a subrectangle spanning 20% to 55% heightwise). For videos where the face is not visible, the method marks the region manually with user input.

The movement of the head throughout the video is measured by selecting and tracking feature points within the region. The method can the OpenCV Lucas Kanade tracker between frame 1 and each frame t=2 . . . T to obtain the location time-series $\langle x_n(t) y_n(t) \rangle$ for each point n. Since a modem ECG device operates around 250 Hz to capture heart rate variability and videos are typically shot at 30 Hz, (or frames per second) a cubic spline interpolation can be applied to increase the sampling rate of each $y_n(t)$ to 250 Hz.

Many of the feature points can be unstable and have erratic trajectories. To retain the most stable features, the method determines the maximum distance (rounded to the nearest pixel) traveled by each point between consecutive frames, and discards points with a distance exceeding the mode of the distribution.

Both the vertical and horizontal components are extracted from each feature point trajectory (e.g., $x_1(t)$, $y_1(t)$, $x_N(t)$, $y_N(t)$) where N is the total number of feature points) (204). In other embodiments, however, the method may extract a vertical component, a horizontal component, or a different component.

Each trajectory is then temporally filtered to remove extraneous frequencies that may be outside the range of possible pulse rates (206). Not all frequencies of the trajectories are required or useful for pulse detection. A normal adult's resting pulse rate falls within the range of [0.75, 2] Hz, or [45, 120] beats/min. Frequencies lower than 0.75 Hz can negatively affect the method's performance, because low-frequency movements like respiration and changes in posture have high amplitude and dominate the trajectories of the feature points. However, harmonics and other frequencies higher than 2 Hz provide useful precision needed for peak detection. Taking these elements into consideration, each $y_n(t)$ is filtered to a passband of [0.75, 5] Hz. The method employs a 5th order butterworth filter for its maximally flat passband.

Principal Component Analysis (PCA) decomposes the trajectories into a set of independent source signals ($s1(t)$, $s2(t)$ . . . $s5(t)$) that describe the main elements of the head motion (208). The underlying source signal of interest is the movement of the head caused by the cardiovascular pulse. The feature point trajectories are a mixture of this movement as well as other motions caused by sources like respiration, vestibular activity and changes in facial expression. The method decomposes the mixed motion into subsignals to isolate pulse by considering the multidimensional position of the head at each frame as a separate data point and using PCA to find a set of main dimensions along which the position varies. The method then selects a dimension on which to project the position time-series to obtain the pulse signal.

Formally, given N feature points, the methods represent the N-dimensional position of the head at frame t as $m_t=[y_1(t), y_2(t), \ldots y_n(t)]$. The mean and the covariance matrix of the positions are:

$$m = \frac{1}{[T]} \sum_{t=1}^{T} m_t \tag{1}$$

$$\sum_m = \frac{1}{T} A \sum_{t=1}^{T} (m_t - m)(m_t - m)^T \tag{2}$$

PCA finds the principal axes of variation of the position as the eigenvectors of the covariance matrix:

$$\Sigma_m \phi_m = \phi_m \Lambda_m \tag{3}$$

where $\Lambda_m$ denotes a diagonal matrix of the eigenvalues $\lambda_1$, $\lambda_d, \ldots, \lambda_N$ corresponding to the eigenvectors in the columns of $\Phi_m$, $\phi_1, \phi_2, \ldots, \phi_N$.

The method selects the component having clearest main frequency, which identifies the average pulse rate (210). Then, peak detection in the time-domain identifies the beats of the selected signal to calculate beat duration (212).

Figure 3:
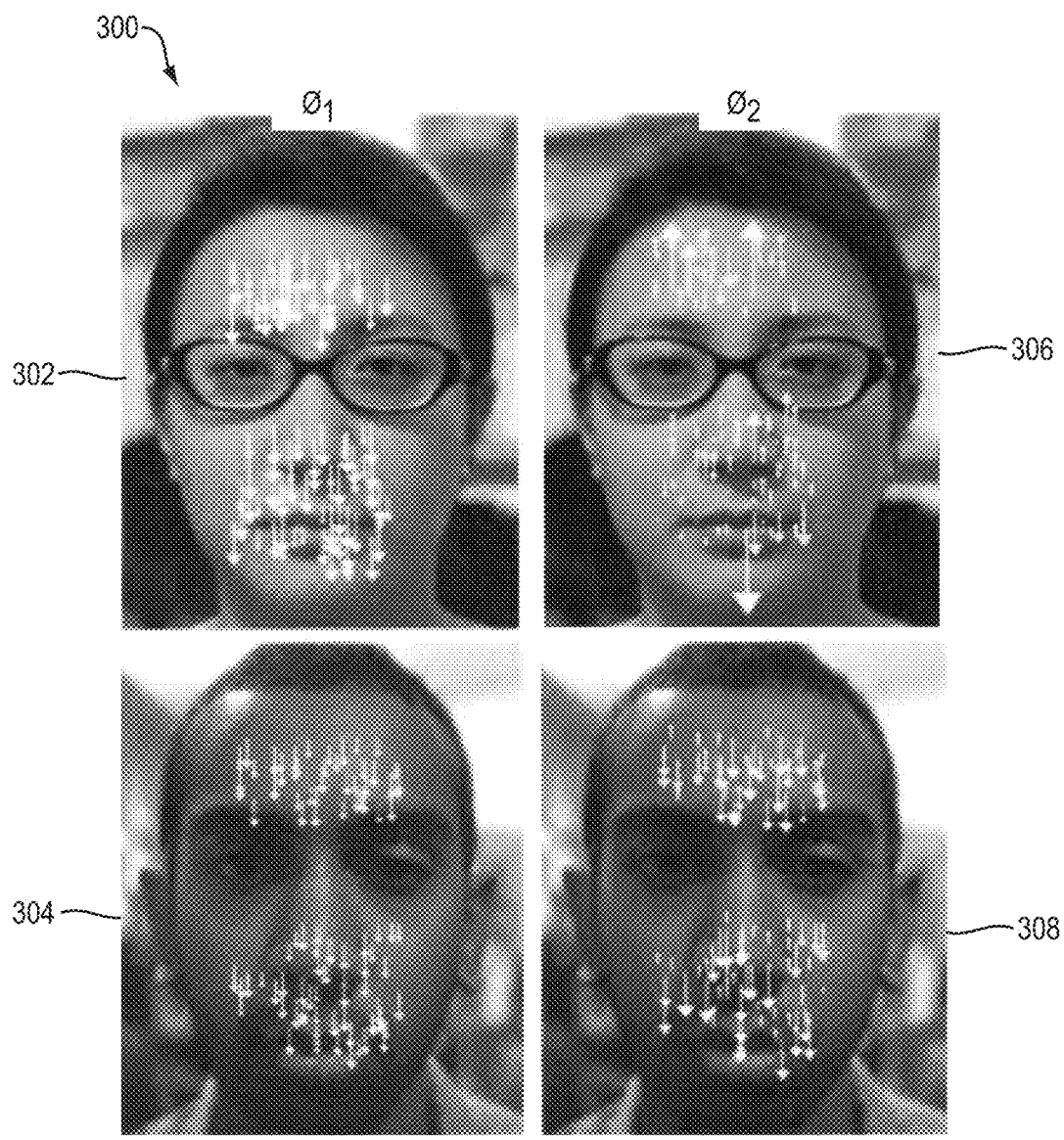
FIG. 3 displays the two eigenvectors ($\phi_1$ and $\phi_2$) for two of the subjects.

FIG. 3 displays the two eigenvectors ($\phi_1$ and $\phi_2$) for two of the subjects (302, 306, and 304, 308, respectively). Each eigenvector, shown as white arrows over the photos of the subjects 302, 304, 306 and 308, represents the N-dimensional direction and magnitude of movement for the feature points. The eigenvectors differ for each subject. The method obtains the one-dimensional (1D) position signal $s_i(t)$ by projecting the position time-series onto $\phi_i$:

$$s_i(t) = \begin{pmatrix} m_1 \\ m_2 \\ \vdots \\ m_t \end{pmatrix} \cdot \phi_i \tag{4}$$

During some periods in the video, the head moves abnormally (e.g., swallowing, adjustments in posture). Such movement adds variance to the position vectors, thereby affecting the PCA decomposition. One way to deal with this is discarding a percentage $\alpha$ of the $m_t$ with the largest L2-norms before performing PCA. However, all of the $m_t$ must still be used in the projection step (Eq. 4) to produce a complete signal. The method sets at 25%.

In an embodiment, an alternative to PCA is independent component analysis (ICA).

The method needs to determine which eigenvector to use for pulse signal extraction. The eigenvectors are ordered such that $\phi_1$ represents the most variance in the data, $\phi_2$ represents the second most, and so on. Although $\phi_1$ represents most of the variance, $s_1$ may not be the clearest pulse signal (e.g., most periodic) for analysis. The method instead chooses the $s_i$ that is most periodic. The method quantifies a signal's periodicity as the percentage of total spectral power accounted for by the frequency with maximal power and its first harmonic.

In an embodiment, it is not necessary to consider any signals beyond the first five, i.e., $s_1, \ldots, s_5$ for any of the subjects. The method labels the maximal frequency of the chosen signal $f_{pulse}$ pulse and approximates the pulse rate as $60 \ast f_{pulse}$ beats per minute.

Average pulse rate alone is not sufficient to fully evaluate the cardiovascular system. Clinicians often assess beat-to-beat variations to form a complete picture. To allow for such analysis, the method performs peak detection on the selected PCA component signal. The peaks are close to $$\frac{1}{f_{pulse}}$$

seconds apart with some pulse variability due to the natural variability of heartbeats, variations of the head motion, and noise. The method labels each sample in the signal as a peak if it is the largest value in a window centered at the sample. The method sets the length of the window (in samples) to be round $$\frac{f_{sample}}{f_{pulse}},$$

where $f_{sample}=250$ Hz.

The method can be implemented in MATLAB, for example. Videos can be shot with a Panasonic Lumix GF2 camera in natural, unisolated environments with varying lighting. The videos can have a frame rate of 30 frames per second, 1280×720 pixel resolution and a duration of 70-90 seconds in one embodiment. Subjects can be connected to a wearable ECG monitor (Delano, M., "A long term wearable electrocardiogram (ECG) measurement system," *Master's Thesis*, Massachusetts Institute of Technology (2012) (hereinafter, "Delano")) to compare the results of the method to the ECG, for testing purposes. This device has a sampling rate of 250 Hz and three electrodes which are placed on the forearms, in one embodiment.

The method extracted pulse signals from 18 subjects with a frontal view of the face (as in FIG. 3). The subjects varied in gender (7 female, 11 male) and skin color. They ranged from 23-32 years of age and were all seemingly healthy. The method calculated the average pulse rate using the frequency of maximal power for the selected PCA component. Similarly, the method computed the true pulse rate by finding the main frequency of the ECG spectrum. Table I presents the results. The average rates are nearly identical to the true rates for all subjects, with a mean error of 1.5%. The number of peaks were also close to ground truth values, with a mean error of 3.4%.

The method evaluates the ability of the signal to capture subtle heart rate variability. Clinically meaningful HRV measures typically use 10-24 hours of ECG data, therefore testing of the method did not attempt to compute any of these for the 90 second videos. Instead, the distributions of time between successive peaks for each signal are compared for testing. Incorrect or missed peaks can introduce spurious intervals too large or small to be caused by the natural variations of the heart. Therefore, only intervals with length within 25% of the average detected pulse period are considered.

The Kolmogorov-Smirnov (KS) test measures the similarity of the distributions, with the null hypothesis being that the observations are from the same distribution. Table 2 presents the results. At a 5% significance level, 16 of the 18 pairs of distributions were found to be similar.

Figure 4:
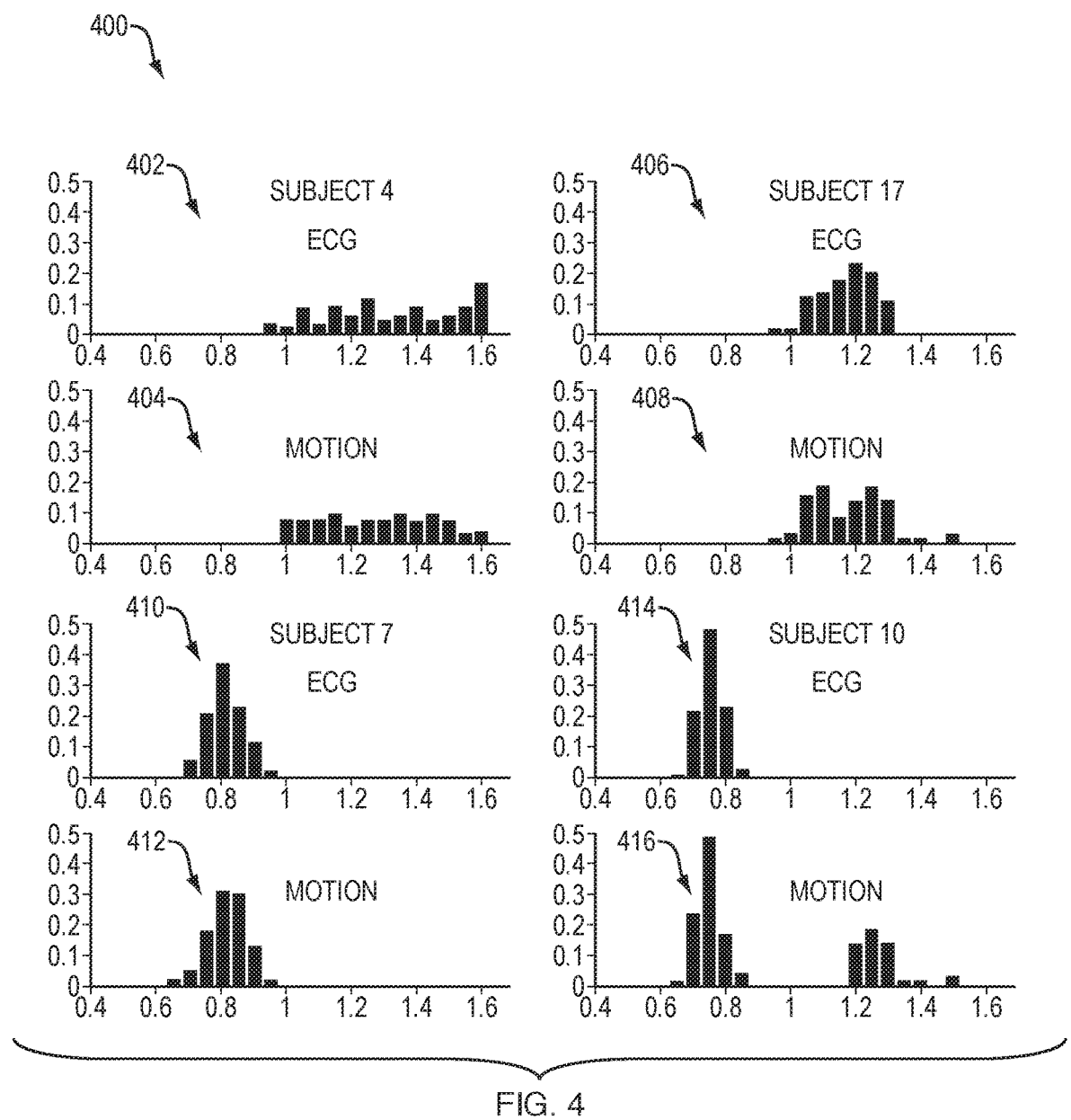
FIG. 4 is a diagram illustrating histograms of four of the 16 distributions binned at every 0.05 seconds.

FIG. 4 is a diagram 400 illustrating histograms of four of the 16 distributions binned at every 0.05 seconds. The method captured a wide range of beat-length distributions shapes, from the flat distribution of subject 4 (402, 404) to the peakier distribution of subject 10 (414, 416). FIG. 4 shows each subject having an ECG histogram (402, 406, 410, 414) being similar to a respective motion based histogram (404, 408, 412, 416) of an embodiment of the present invention

TABLE 1

Average pulse rate and # peaks detected from ECG and by the method.

| | Avg. Pulse (beats per minute) | | Number of beats | |
|---|---|---|---|---|
| Sub. | ECG | Motion(% error) | ECG | Motion(% error) |
| 1 | 66.0 | 66.0(0) | 99 | 98(1.0) |
| 2 | 54.7 | 55.3(1.1) | 82 | 84(2.4) |
| 3 | 81.3 | 82.6(1.6) | 122 | 116(4.9) |
| 4 | 44.7 | 46.0(2.9) | 67 | 70(4.5) |
| 5 | 95.3 | 96.0(0.7) | 143 | 142(0.7) |
| 6 | 78.9 | 78.0(1.1) | 92 | 78(15.2) |
| 7 | 73.3 | 71.3(2.7) | 110 | 100(9.1) |
| 8 | 59.3 | 58.6(1.2) | 89 | 88(1.1) |
| 9 | 56.7 | 58.6(3.4) | 85 | 84(1.2) |
| 10 | 78.7 | 79.3(0.8) | 118 | 117(0.8) |
| 11 | 84.7 | 86.6(2.2) | 127 | 121(4.7) |
| 12 | 63.3 | 62.6(1.1) | 95 | 95(0) |
| 13 | 59.3 | 60.0(1.2) | 89 | 89(0) |
| 14 | 60.0 | 61.3(2.2) | 90 | 89(1.1) |
| 15 | 80.0 | 81.3(1.6) | 120 | 114(5.0) |
| 16 | 74.7 | 74.6(0.1) | 112 | 110(1.8) |
| 17 | 50.0 | 49.3(1.4) | 75 | 76(1.3) |
| 18 | 77.1 | 78.8(2.2) | 90 | 85(5.6) |

Table 2 presents results when comparing the interpeak distributions of the ECG and the method including the means ($\mu$) and standard deviations ($\sigma$) of each distribution, the number of outliers removed from the distribution, and the p-value of distribution similarity. 16 of the 18 pairs of distributions were not found to be significantly different.

TABLE 2

| Sub. | ECG $\mu(\sigma)$ | Motion $\mu(\sigma)$ | KS-Test p-value |
|---|---|---|---|
| 1 | 0.91(0.06) | 0.90(0.06) | 0.89 |
| 2 | 1.08(0.08) | 1.06(0.11) | 0.52 |
| 3 | 0.73(0.04) | 0.73(0.08) | 0.05 |
| 4 | 1.34(0.19) | 1.28(0.18) | 0.14 |
| 5 | 0.62(0.03) | 0.63(0.07) | <0.01 |
| 6 | 0.76(0.04) | 0.76(0.04) | 0.64 |
| 7 | 0.81(0.05) | 0.81(0.06) | 0.85 |
| 8 | 1.01(0.04) | 1.02(0.09) | 0.16 |
| 9 | 1.04(0.07) | 1.04(0.11) | 0.27 |
| 10 | 0.75(0.04) | 0.75(0.04) | 0.75 |
| 11 | 0.70(0.06) | 0.70(0.08) | 0.30 |
| 12 | 0.94(0.08) | 0.94(0.09) | 0.85 |
| 13 | 0.99(0.04) | 0.98(0.12) | <0.01 |
| 14 | 0.99(0.11) | 0.98(0.12) | 0.47 |
| 15 | 0.74(0.05) | 0.75(0.06) | 0.95 |
| 16 | 0.80(0.05) | 0.80(0.06) | 0.60 |
| 17 | 1.18(0.08) | 1.18(0.11) | 0.70 |
| 18 | 0.76(0.05) | 0.76(0.06) | 0.24 |

Pulse motion constitutes only a part of total involuntary head movement. The magnitude of the different movements within [0.75, 5] Hz is quantified by calculating root mean square (RMS) amplitudes of the feature point trajectories. For each subject, the mean RMS amplitude of the trajectories is calculated before and after filtering to a passband within 5% of the pulse frequency. The mean RMS amplitude of the trajectories without filtering was 0.27 (std. dev of 0.07) pixels across the subjects. The mean RMS amplitude after filtering to the pulse frequency was 0.11 (0.05) pixels. Thus, the pulse motion had roughly 40% the RMS amplitude of other head motions within the [0.75, 5] Hz frequency range. The robustness of the method can be compared to a color-based pulse detection system (Poh, M. et al.) in the presence of noise. The color method spatially averages the R, G, and B channels in the facial area and uses independent component analysis (ICA) to decompose the signals into three independent source signals. The source with the largest peak in the power spectrum is then chosen as the pulse signal.

Varying levels of zero-mean Gaussian noise can be added to the videos and swept the standard deviation from 5 to 500 pixels. For each subject, $\sigma_{motion}$, the maximum noise standard deviation, was calculated before the method first produced an average pulse rate outside 5% of the true rate. $\sigma_{color}$ was calculated in a similar manner for the color method.

Figure 5:
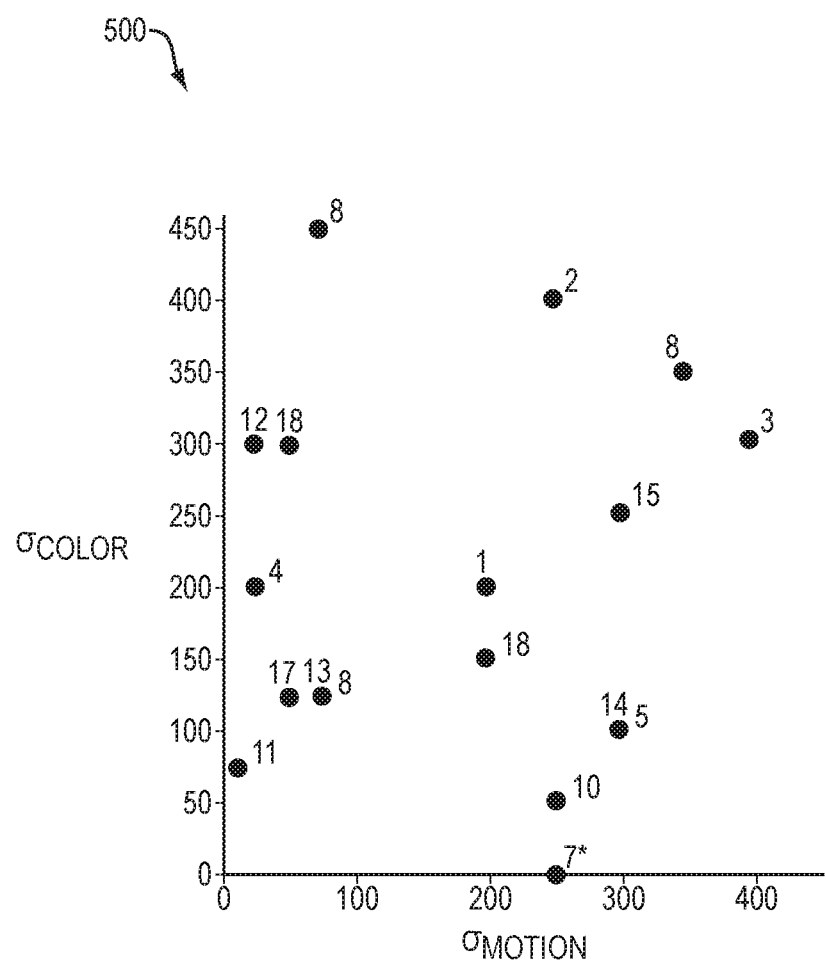
FIG. 5 is a diagram illustrating the results of the subjects, plotting $\sigma_{color}$ based on $\sigma_{motion}$.

FIG. 5 is a diagram 500 illustrating the results of the subjects, plotting $\sigma_{color}$ based on $\sigma_{motion}$. Each point represents one of the results of the subjects $\sigma_{color}$ value based on $\sigma_{motion}$. The method outperformed color for seven of the seventeen subjects, and performed worse for nine subjects. Note that color failed to produce a correct pulse rate for subject seven before adding any noise.

There is a large variance in $\sigma_{motion}$ and $\sigma_{color}$ across the subjects, suggesting that there are subject-specific factors that affect performance. To understand why, $\sigma_{motion}$ is compared to to $\beta$, the ratio of the total energy of the feature points within 5% of $f_{pulse}$ to the maximal energy at any other frequency.

Figure 6:
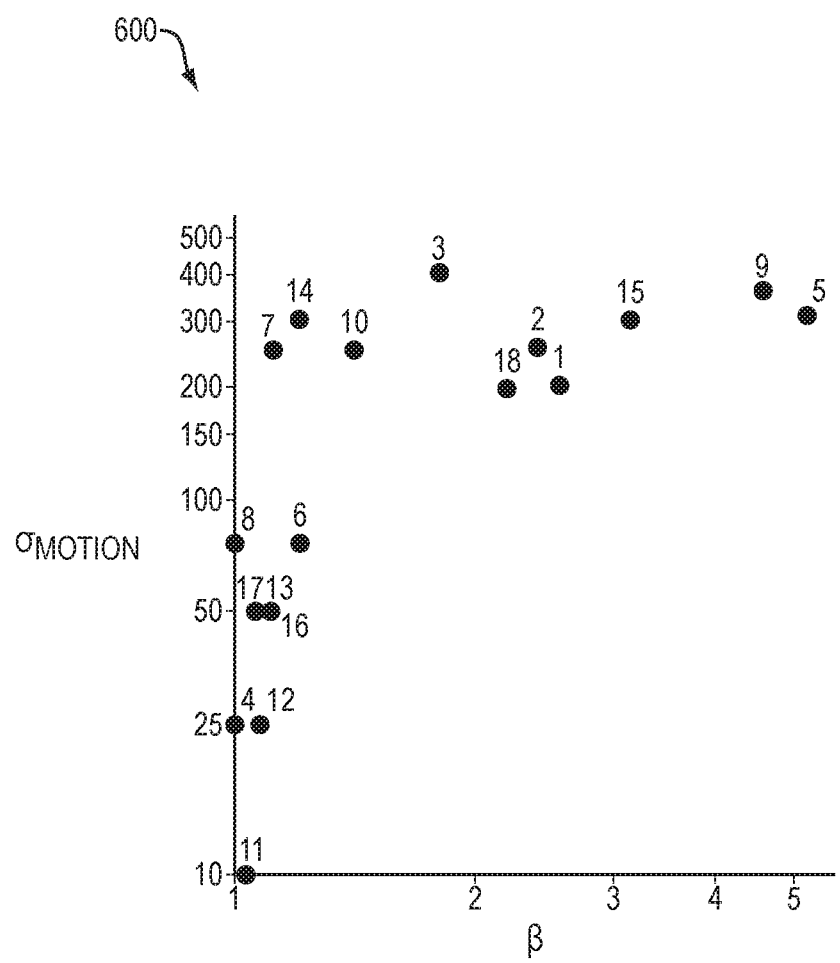
FIG. 6 is a graph illustrating a plot of $\sigma_{motion}$ against $\beta$ for all subjects on a logarithmic scale.

FIG. 6 is a graph 600 illustrating a plot of $\sigma_{motion}$ against $\beta$ for all subjects on a logarithmic scale. The subjects with the 10 highest $\sigma_{motion}$ values also have 10 of the top 11 $\beta$ values. This indicates that the method performs best for subjects with a large ballistocardiac motion relative to any other periodic head movement.

No similar relationship between $\sigma_{color}$ and the frequency content of the Red, Green, and Blue (RGB) channels was found, likely because of the layer of complexity introduced by the ICA algorithm. However, when simplifying the method to extracting a signal from the G channel alone, noise performance is shown to be strongly related to the ratio of power at the pulse frequency to the next largest power in the spectrum. No relationship was found between motion or color performance and skin tone.

Figure 7:
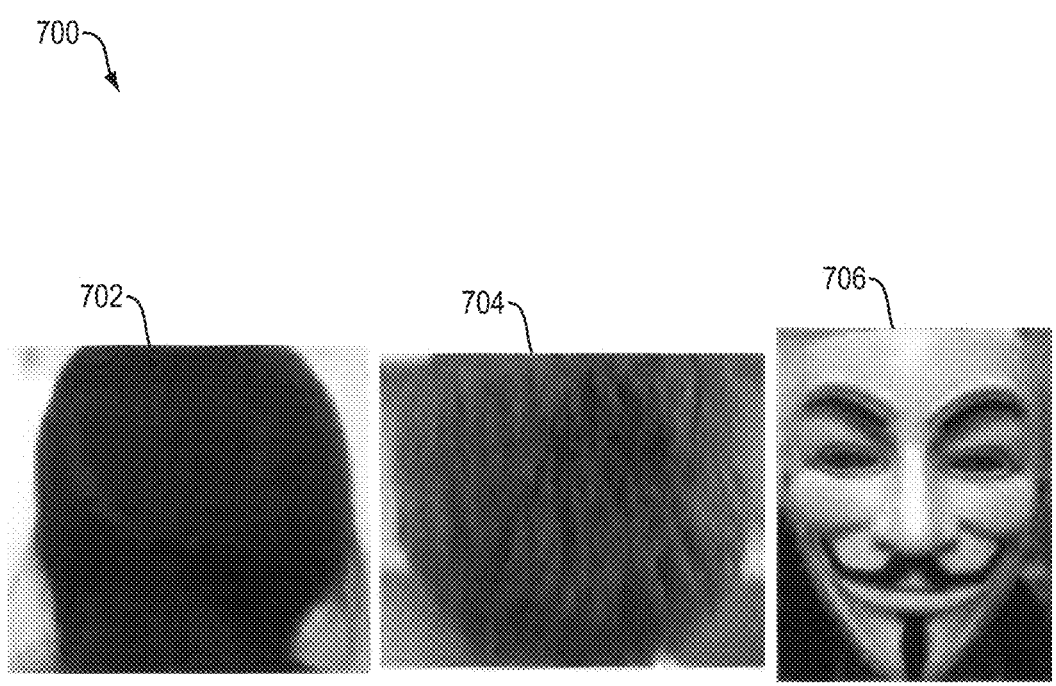
FIG. 7 are frames from videos employed by an embodiment of the present invention.

FIG. 7 are frames 702, 704, and 706 from videos employed by an embodiment of the present invention. One advantage of motion-based detection over color is that a direct view of the skin is not needed. Videos of the backs of the heads (702, 704) of eleven subjects and a video of one subject wearing a mask (706), as shown in FIG. 7, were able to produce average heart rates close to the true values for all videos.

Figure 8:
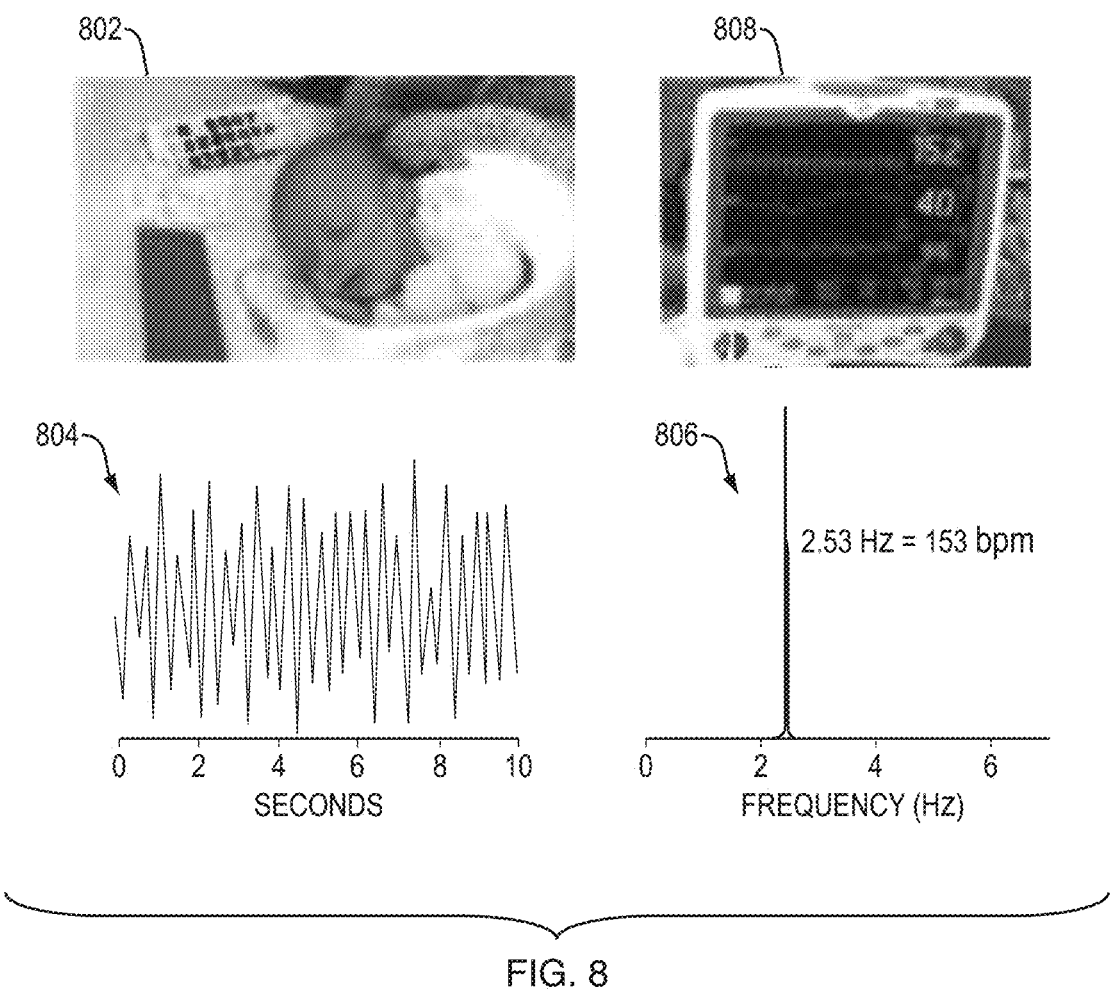
FIG. 8 is a diagram showing a frame from a 30-second video of a newborn recorded in situ at a hospital nursery and corresponding graphs.

FIG. 8 is a diagram showing a frame 802 from a 30-second video of a newborn recorded in situ at a hospital nursery and corresponding graphs 804 and 806. A video of the baby's actual pulse rate is shown on a hospital-grade monitor 808 measuring the perfusion of blood to its skin. The method extracts a clean pulse signal 804 and a corresponding frequency response that matches the pulse rate reported by the monitor.

Embodiments of the present invention consistently obtain accurate pulse rate measurements from head motion. The results for beat detection are equally encouraging. Most beat interval distributions looked qualitatively similar to the ECG distributions, indicating that the method captures a real physiological variability. For sixteen of the eighteen subjects, there is no statistically significant difference between the ECG and the motion beat intervals. This is a stronger test than is required in most clinical contexts. Typically heart rate variability (HRV) is used to dichotomize patients into high and low risk groups, so the precise shape of the distribution is not relevant. The relevant test is whether the distribution of motion-generated intervals yields the same set of high risk individuals as ECG generated intervals. Since all subjects were healthy volunteers, high risk individuals were not tested.

Several factors affected the results. First, the camera has a sampling rate of 30 Hz. ECG used for HRV analysis normally has a sampling rate of at least 128 Hz. Cubic interpolation of the signal only partially addresses this discrepancy. Second, extra variability might be introduced during the pulse transit time from the abdominal aorta to the head. In particular, arterial compliance and head mechanics could affect the results. Third, the variable and suboptimal lighting conditions can affect the feature tracking. Finally, the videos were only a maximum of 90 seconds long. Normally, HRV measures are computed over many hours to obtain reliable estimates.

An important future direction is to develop approaches for moving subjects. This is complicated because, as the results show, even other involuntary head movements are quite large in relation to pulse motion. Clearly with larger motions such as talking, more sophisticated filtering and decomposition methods are needed to isolate pulse.

This method considers the frequency and variability of the pulse signal. However, head movement can offer other information about the cardiac cycle. If head displacement is proportional to the force of blood being pumped by the heart, it may serve as a useful metric to estimate blood stroke volume and cardiac output. Additionally, the direction of the movement could reveal asymmetries in blood flow into or out of the head. This might be useful for the diagnosis of a stenosis, or blockage, of the carotid arteries.

Another future direction is to better assess the strengths and weaknesses of the color and motion pulse estimation methods. The results suggest that neither method is strictly more robust than the other in the presence of noise. However, further work needs to be done with varying lighting, skin tones, and distance from the camera to form a complete picture. In addition, sensitivity of the method to voluntary motions like talking or typing. For many applications, this is a critical factor. A motion-based approach is certainly better when the face is not visible. Based on these ideas, a combination of the color and motion methods are more useful and robust than using either one independently.

The present invention offers a non-invasive, non-contact means of cardiac monitoring. The method takes video as input and uses feature tracking to extract heart rate and beat measurements from the subtle head motion caused by the Newtonian reaction to the pumping of blood at each heartbeat. A combination of frequency filtering and PCA allows identification of the component of motion corresponding to the pulse and then extraction of peaks of the trajectory to identify individual beats. When evaluated on eighteen subjects, the method produced virtually identical heart rates to an ECG and captured some characteristics of inter-beat variability.

Figure 9:
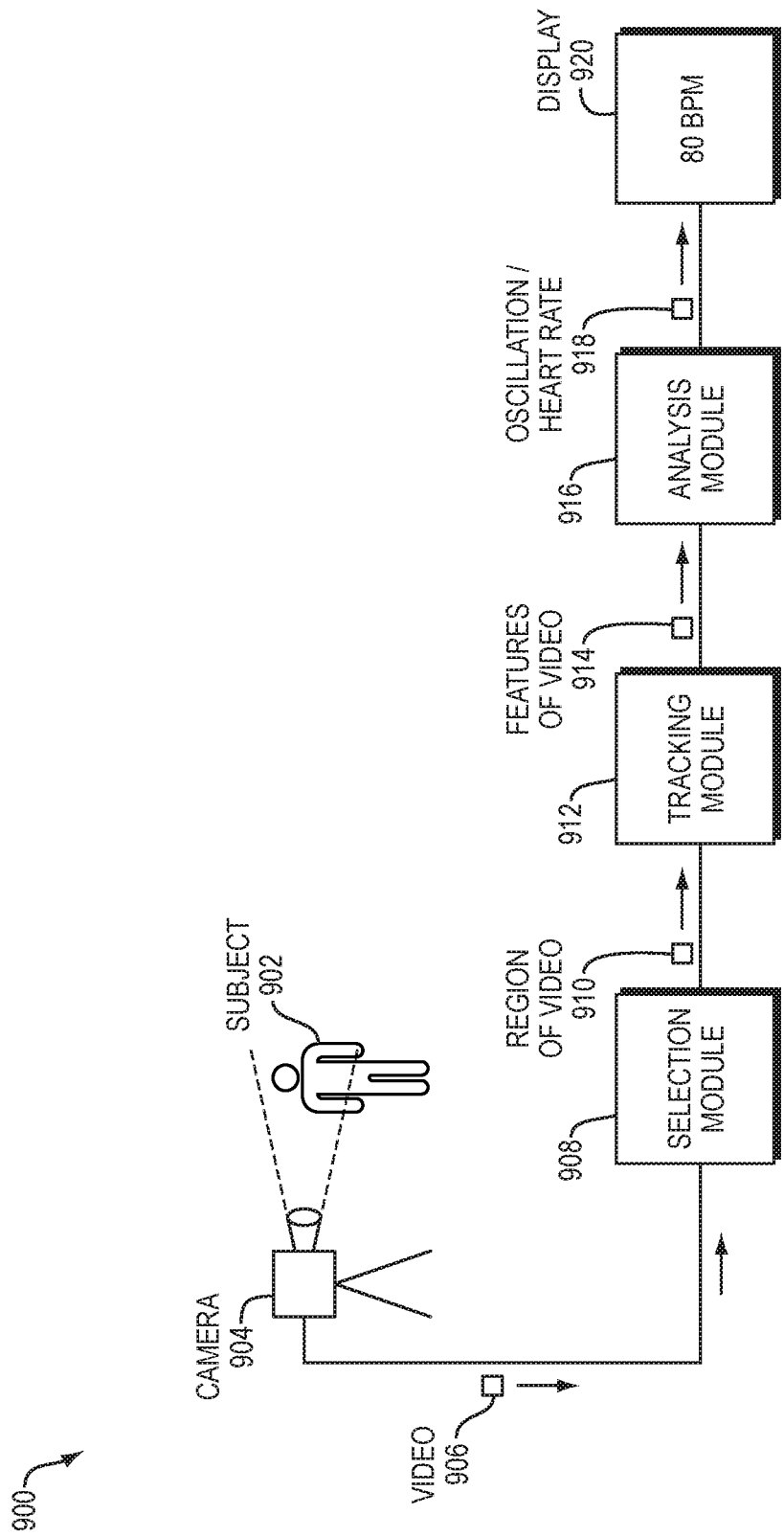
FIG. 9 is a block diagram illustrating an example embodiment of the present invention.

FIG. 9 is a block diagram 900 illustrating an example embodiment of the present invention. A subject 902 is videotaped by a camera 904 for a period of time, recording a video 906 having the subject's 902 head in the frame. A selection module 908 receives the video 906 recorded by the camera 904 directly or via in intermediary. The selection module 908 selects a region of the video 910 having the subject's head and forwards it to a tracking module 912. The selection of the region of the video 910 is described above. The tracking module 912 then tracks features of the video 914 which are forwarded to the analysis module 916. The analysis module calculates an oscillation or heart rate 918 based on the features 914, which it outputs to a display 920.

Embodiments or aspects of the present invention may be implemented in the form of hardware, software, or firmware. If implemented in software, the software may be any form of software capable of performing operations consistent with the example embodiments disclosed herein. The software may be stored in any non-transitory computer readable medium, such as RAM, ROM, magnetic disk, or optical disk. When loaded and executed by processor(s), the processor(s) are configured to perform operations consistent with the example embodiments disclosed herein. The processor(s) may be any form of processor(s) capable of being configured to execute operations as disclosed herein.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A computer-implemented method of monitoring vital signs comprising:
   in a digital processor:
   receiving an input video of an upper body portion of a subject, the input video being formed of a sequence of frames, each frame: (i) providing a respective image of the upper body portion, (ii) having spatial locations corresponding to feature points in the image, and (iii) representing a data point in a position-time series of the sequence of frames, each location being a pixel representing visible light spectrum;
   forming a location-time series returning the spatial locations of each feature point across plural frames of the input video; and
   from the formed location-time series and the position-time series, detecting a pulse signal and extracting pulse rate measurements, said extracting including output of a pulse rate or a heart rate of the subject shown in the video.

2. The method of claim 1, wherein the upper body portion is a head of the subject, and the input video captures movement of the head.

3. The method of claim 2, wherein for each frame, the data point represents position of the head in the position-time series.

4. The method of claim 2, wherein detecting the pulse signal includes:
   isolating from the formed location-time series motion of the head corresponding to pulse, said isolating resulting in a component of the location-time series of the feature points that correspond to pulse; and
   projecting the resulting component onto a one-dimensional signal in a manner that allows extraction of individual beat boundaries.

5. The method of claim 2, wherein each frame represents a multidimensional position of the head; and
   wherein detecting the pulse signal: (i) utilizes principal component analysis on the formed location-time series and finds a set of main dimensions along which the position of the head varies; and (ii) selects a dimension on which to project the position-time series to obtain the pulse signal.

6. The method of claim 2, wherein the detecting includes:
   temporally filtering the formed location-time series;
   identifying component of motion of the head corresponding to pulse using principal component analysis on the temporally filtered location-time series; and
   identifying individual beats of the pulse signal by extracting peaks of the temporally filtered location-time series.

7. The method of claim 6, wherein temporally filtering the formed location-time series removes frequencies that are outside a predetermined range of pulse rates.

8. The method of claim 6, wherein performing principal component analysis includes decomposing the filtered location-time series into a set of independent source signals.

9. The method of claim 1, wherein detecting the pulse signal includes: (a) extracting peaks of the formed location-time series, and (b) from the extracted peaks, identifying individual beats and calculating beat duration.

10. The method of claim 1, wherein the detecting and extracting further results in output of heart beat sequences of the subject.

11. A system monitoring vital signs comprising:
    a computer processor coupled to receive an input video of an upper body portion of a subject, the input video being formed of a sequence of frames, each frame: (i) providing a respective image of the upper body portion, (ii) having spatial locations corresponding to feature points in the image, and (iii) representing a data point in a position-time series of the sequence of frames, each location being a pixel representing visible light spectrum;
    a tracking module executable by the processor and configured to form a location-time series returning the spatial locations of each feature point across plural frames of the input video; and
    an analyzer implemented by the processor and configured to responsively detect a pulse signal and extract pulse rate measurements from the formed location-time series and the position-time series, the analyzer outputting a pulse rate or a heart rate of the subject in the input video.

12. The system of claim 11, wherein the upper body portion is a head of the subject, and the input video captures movement of the head.

13. The system of claim 12, wherein for each frame, the data point represents position of the head in the position-time series.

14. The system of claim 12, wherein the analyzer detecting the pulse signal includes the analyzer being configured to:
    isolate from the formed location-time series motion of the head corresponding to pulse, said isolating resulting in a component of the location-time series of the feature points that correspond to pulse; and project the resulting component onto a one-dimensional signal in a manner that allows extraction of individual beat boundaries.

15. The system of claim 12, wherein each frame represents a multi-dimensional position of the head; and
wherein the analyzer: (i) utilizes principal component analysis on the formed location-time series to find a set of main dimensions along which the position of the head varies; and (ii) selects a dimension on which to project the position-time series to obtain the pulse signal.

16. The system of claim 12, wherein the analyzer is further configured to:
temporally filter the formed location-time series;
identify component of motion of the head corresponding to pulse using principal component analysis on the temporally filtered location-time series; and
identify individual beats of the pulse signal by extracting peaks of the temporally filtered location-time series.

17. The system of claim 16, wherein the analyzer is further configured to filter the formed location-time series temporally by removing frequencies that are outside a predetermined range of pulse rates.

18. The system of claim 16, wherein the analyzer is further configured to perform principal component analysis by decomposing the filtered location-time series into a set of independent source signals.

19. The system of claim 11, wherein the analyzer detecting and extracting further results in output of heartbeat sequences of the subject.

20. A non-transitory computer readable medium comprising:
a memory area having program code stored thereon; and
the program code including instructions which when loaded and executed by a processor cause the processor to:
receive an input video of at least a head of a subject, the input video being formed of a sequence of frames, each frame: (i) providing a respective image of the subject, (ii) having spatial locations corresponding to feature points in the image, and (iii) representing a data point in a position-time series of the sequence of frames, each location being a pixel representing visible light spectrum;
form a location-time series returning the spatial locations of each feature point across plural frames of the input video; and
from the formed location-time series and the position-time series, detect a pulse signal and extract pulse rate measurements, said extracting including output of a pulse rate or a heart rate of the subject shown in the video.

* * * * *